United States Patent [19]

Costantini et al.

[11] 4,250,330
[45] Feb. 10, 1981

[54] PROCESS FOR THE RECOVERY OF THE SOLVENT AND OF THE BY-PRODUCED METHYLACETATE IN THE SYNTHESIS OF TEREPHTHALIC ACID

[75] Inventors: Giuseppe Costantini, Mogliano Veneto; Mauro Serafini, Milan; Pietro Paoli, Carpenedo-Mestre, all of Italy

[73] Assignee: Montedison S.p.A., Milan, Italy

[21] Appl. No.: 116,851

[22] Filed: Jan. 30, 1980

Related U.S. Application Data

[63] Continuation of Ser. No. 892,195, Mar. 31, 1978, abandoned.

[30] Foreign Application Priority Data

Apr. 13, 1977 [IT] Italy ............................... 22408 A/77

[51] Int. Cl.$^3$ .................... C07C 51/255; C07C 67/00; C07C 67/48; B01D 3/34
[52] U.S. Cl. .................................. 562/409; 562/414; 562/416; 560/241; 560/248; 203/60
[58] Field of Search ....................... 562/409, 414, 416; 560/241, 248

[56] References Cited

U.S. PATENT DOCUMENTS 2,833,817   5/1958   Saffer .................................... 562/414
3,487,108   12/1969  Chibnik ................................. 562/417

Primary Examiner—Alan Siegel
Attorney, Agent, or Firm—Morgan, Finnegan, Pine, Foley & Lee

[57] ABSTRACT

The invention refers to an improved process for the recovery of the solvent and of the by-produced methylacetate in the synthesis of terephthalic acid, said synthesis being usually consisting of an oxidation of paraxylene with air, in the presence of a catalyst system composed by cobalt, manganese and bromine, in a solvent consisting of acetic acid, according to the equation (1):

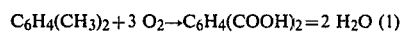

$$C_6H_4(CH_3)_2 + 3\ O_2 \rightarrow C_6H_4(COOH)_2 = 2\ H_2O \quad (1)$$

More particularly, the improved process of this invention comprises the oxidation of para-xylene in acetic acid solution and in the presence of a catalytic system based on manganese, bromine and cobalt, whereby water is formed and methylacetate is by-produced during the oxidation, whereby solid terephthalic acid is separated from the mother liquor and whereby one withdraws from the oxidation zone a liquid which is obtained by condensing the vapors released during the oxidation and which are mainly consisting of acetic acid and water, the improvement consisting of the fact that:
(a) the liquid obtained by condensing the released vapors and said mother liquor are fed both to an azeotropic distillation system in which the azeotropic agent is isobutyl-acetate;
(b) the light ends of the azeotropic distillation, richer in water, are condensed and demixed into two phases, wherein the aqueous phase, which is lower and contains isobutyl-acetate and methyl-acetate, is conveyed to a stripping, whereby isobutyl-acetate and methylacetate are recovered, and wherein the organic phase is recycled to the azeotropic distillation.

7 Claims, 2 Drawing Figures 4,250,330

PROCESS FOR THE RECOVERY OF THE SOLVENT AND OF THE BY-PRODUCED METHYLACETATE IN THE SYNTHESIS OF TEREPHTHALIC ACID

CROSS-REFERENCE TO RELATED APPLICATION

This is a continuation of application Ser. No. 892,195, filed Mar. 31, 1978, now abandoned.

BACKGROUND OF THE INVENTION

In the prior art method illustrated by equation (1), the reaction water dilutes the acid and inhibits the oxidation, which cannot be considered as a satisfactory synthesis from an industrial viewpoint when the water content exceeds 30%, and sometimes even only 20% by weight of the reacting mixture. Besides the necessity to keep the acetic acid anhydrous there is the necessity, in this type of synthesis, to recover the acetic acid from the more or less dilute solutions which are originated in various parts of the plant, as for example the mother liquor coming from the centrifuges where the solid terephtalic acid is separated. Until now the different aqueous-acetic solutions were fed to a rectification column, where a great number of trays and a high reflux ratio allowed to obtain almost anhydrous acetic acid (on the column bottom) and water containing acetic residues (at the column top). The distillations performed so far, are not free from drawbacks; in fact they involve:

(a) a great number of trays (in some cases up to 80) and an excessive steam consumption, in order to obtain, at the column top, a water stream containing no more than from 1000 to 5000 ppm of acetic acid and, on the column bottom, an anhydrified acid stream containing no more than 3% by weight of water;

(b) the total loss of the methyl-acetate leaving the column top along with water.

OBJECTS OF THE INVENTION

It is an object of the present invention to reduce the drawbacks of the prior art processes mentioned hereinabove. Further objects will be apparent from the following description.

SUMMARY OF THE INVENTION

A process for the synthesis of terephtalic acid, comprising the oxidation of para-xylene in acetic acid solution and in the presence of a catalytic system based on manganese, bromine and cobalt, whereby water is formed and methyl-acetate is by-produced during the oxidation, whereby solid terephtalic acid is separated from the mother liquor and whereby one withdraws from the oxidation zone a liquid which is obtained by condensing the vapours released during the oxidation and which are mainly consisting of acetic acid and water, the improvement consisting of the fact that:

(a) the liquid obtained by condensing the released vapours and said mother liquor are fed both to an azeotropic distillation system in which the azeotroping agent is isobutyl acetate;

(b) the light ends of the azeotropic distillation, richer in water, are condensed and demixed into two phases, wherein the aqueous phase, which is lower and contains isobutyl-acetate and methyl-acetate, is conveyed to a stripping, whereby isobutyl-acetate and methyl-acetate are recovered, and wherein the organic phase is recycled to the azeotropic distillation.

GENERAL DESCRIPTION OF THE INVENTION

In its broadest form the invention refers to a method of recovering and anhydrifying the solvent and of recoverng methyl-acetate as by-product, in a process for synthetising terephtalic acid, said synthesis comprising the oxidation of paraxylene, in the presence of cobalt, manganese and bromine, within a solvent consisting of acetic acid; such method is characterized in that the different aqueous-acetic solutions which are originated during said process are fed to an azeotropic distillation system, in which the azeotroping agent is isobutyl acetate.

Isobutyl acetate (boiling point about 117° C.; latent heat about 74 Kcal/Kg; forms an azeotropic mixture with water containing 16.5% by weight $H_2O$ and boiling at 87.4° C.) exhibited an exceptional compatibility with the oxidation reaction and the lowering of the steam consumption exceeds what was expectable on the basis of calculations. Furthermore, isobutyl acetate has proved extremely effective in allowing the recovery of methyl-acetate (boiling point about 57° C.; latent heat about 98 Kcal/Kg; forms an azeotropic mixture with water containing 2.5% by weight of water and boiling at 56.5° C.); methyl-acetate can be thus recovered as an aqueous solution at 80 and even at 90% by weight. Simultaneously, the last traces of unconverted paraxylene, entrained through the various process steps, are recovered. Another advantage consists in an extraordinary reduction of the apparatuses' dimensions, equal results being nevertheless obtained; this is particularly evident when the solutions to be distilled are very dilute.

Reference will now be made to the drawings to further described the invention.

Figure 1:
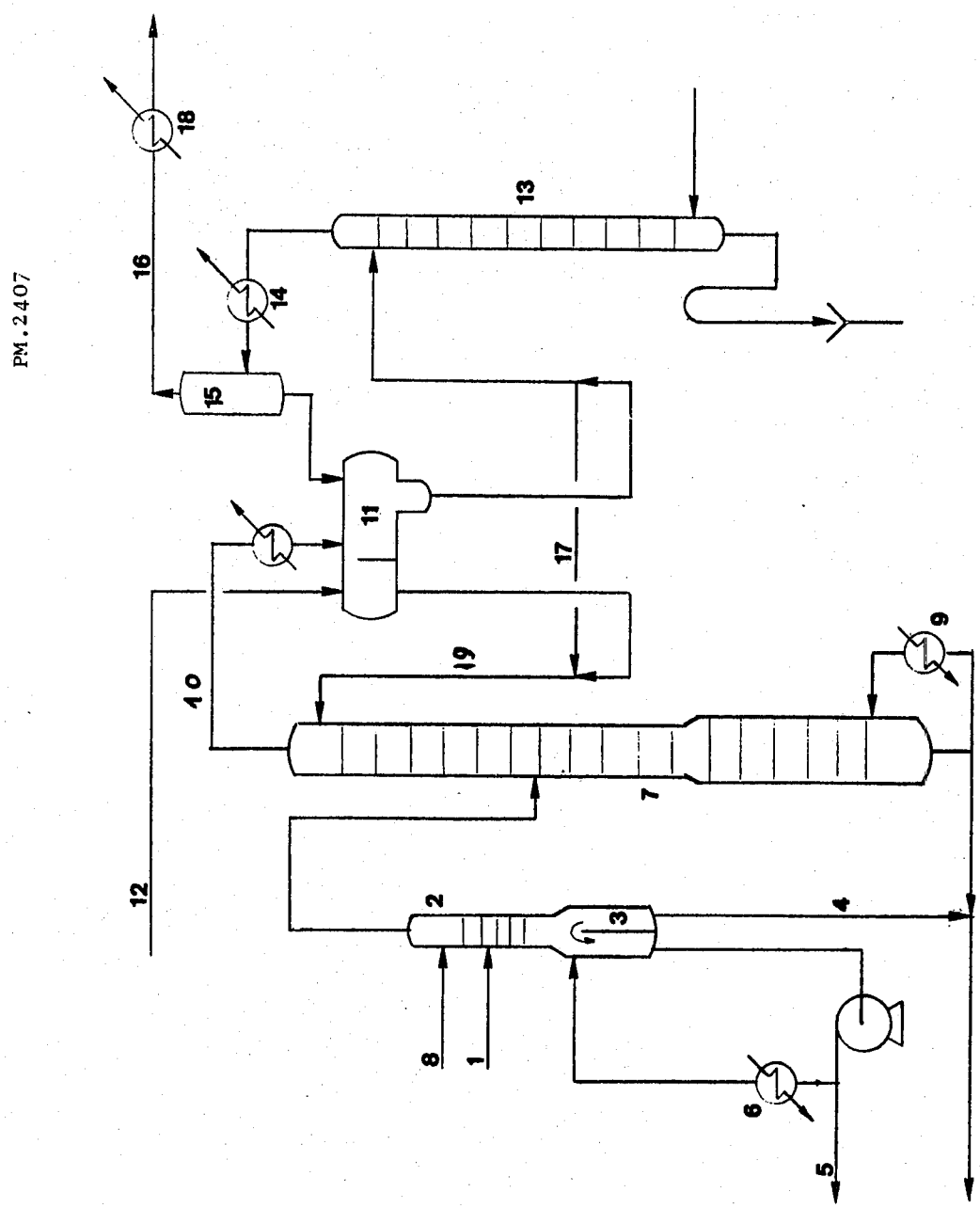
FIG. 1 is a flow diagram of a process for the production of terephthalic acid according to the instant claims.

According to FIG. 1, the effluent (10) from the top of an azeotropic distillation column is condensed and demixed into two phases, the aqueous phase being fed to a stripping column (13) for the recovery of isobutyl acetate. The effluent from the top of the stripping column is partially condensed and fed to a separator (15); the liquid phase, consisting substantially of isobutylacetate, is recycled to the azeotropic distillation column, while the vapour phase (16), prevailingly consisting of methyl-acetate, is first condensed and subcooled and then collected in a storage tank. The water leaving the stripping column bottom contains extremely low percentages of organic matters, by far lower than the values determined so far in processes of this type. This excellent and unexpected results make easier the operations to be carried out downstream for the safeguard of the ecological estate.

The reflux ratio between the amount of isobutyl acetate recycled through line (19) and the amount of water in the effluent (10) should be preferably from 4:1 to 14:1 by weight and more preferably from 6:1 to 10:1.

Useful variations may be made within the scope of the present invention. For example, the purge (line 5 in FIG. 1) should preferably be highly concentrated; prior to the isolation and regeneration treatments it is advisable to use preferably thin layer heat exchangers, optionally equipped with rotary stirrers, coaxial with the down-coming film. Recycle (4) shall contain less than 10%, preferably less than 5% by weight of water, a manganese amount ranging from 50 to 1000 mg/Kg of acetic acid (i.e., from 0.005 to 0.100% by weight) and a cobalt amount corresponding to a manganese:cobalt ratio from 2:1 to 4:1 by weight; the residence time of the mother liquor in the column (excluding the long residence time in the still pot) shall be less than 30 minutes and preferably less than 10 minutes. Furthermore, the bromine:(manganese+cobalt) ratio should be suitably comprised between 0.5 and 2 by weight, preferably between 0.5 and 1.5; iron should be present in amounts never exceeding 50 mg/Kg of acetic acid. A particular and useful method of preparing the catalytic system is disclosed in Italian patent application No. 26,113 A/77 in the name of the Applicant.

Other details concerning the oxidation of paraxylene are found in Italian patent application No. 22,058 A/77, also in the name of the Applicant.

This application discloses a process for the synthesis of terephthalic acid, in which water and methyl acetate are also formed, comprising the oxidation of paraxylene in acetic acid solution at a temperature of from 100° to 230° C., at a pressure from 1 to 30 kg/cm$^2$, and in the presence of a catalytic system based on manganese, bromine and cobalt.

SPECIFIC DESCRIPTION OF THE INVENTION

The following examples are given in order to illustrate the invention, without being however a limitation thereof.

EXAMPLE 1

According to FIG. 1, the mother liquor was fed, through pipe (1), to a partially anhydrifying column equipped with 5 trays; said column had a bottom of enlarged diameter; this bottom was linked to the upper cylindrical section by means of a frusto conical surface and was divided into two parts by a vertical wall; the first part was arranged under the downcomer of the bottom tray, and from said first part the recycle (4) was directly drawn for the oxidation. Such recycle contained about 50% of the catalytic system entering the common (cobalt, manganese and bromine) and about 60% of the acetic acid necessary as a solvent for the oxidation; the water content in said recycle was approximately equal to 3% by weight. Concentrated purge (5) contained the remaining portion of the catalytic system, but only a small amount of acetic acid, as exchanger (3) caused the release of the acetic acid vapours necessary for the distillation; also a liquid stream (8) of aqueous acetic acid at 70% (by weight), coming from other parts of the plant, entered the top of the column (2). The process illustrated so far is described also in Italian patent application No. 22,058 A/77, in the name of the Applicant.

Figure 2:
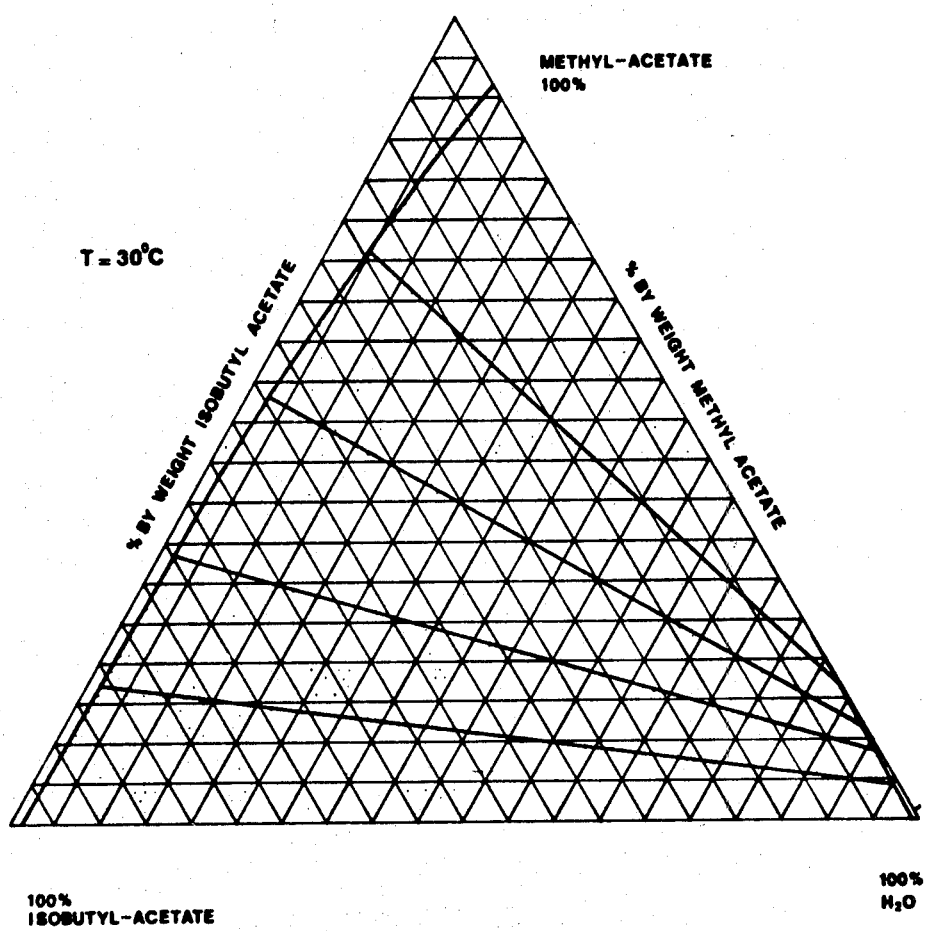
FIG. 2 is a ternary diagram concerning the miscibility and immiscibility of compositions comprising water, methyl acetate and isobutyl-acetate.

The vapours (10) leaving the column top entered a second tray column, equipped with a reboiler, a reflux condenser and a demixing tank (11). Through pipe (12), an amount of an azeotropic agent (isobutyl-acetate), sufficient to make up for the losses, was added to the reflux condenser; a vertical baffle arranged in tank (11) permitted to easily separate the organic phase (that flowed back to the column top) from the aqueous phase. Successively isobutyl-acetate, methyl-acetate and other organic compounds were recovered by means of a stripping with direct steam in a column (13), supplied with a partial condenser. A tank (15) separated the uncondensed vapour phase (16), consisting for the 92% of methyl-acetate, from a liquid phase predominantly consisting of isobutyl-acetate, that passed to the demixing tank (11). The vapour phase, predominantly consisting of methyl-acetate, was condensed in exchanger (18) and sent to storage. The water flowing out from the stripping column bottom was discharged and resulted to be extremely poor in organic matters; actually it contained only 30 ppm of acetic acid and 20 ppm of isobutyl acetate, against 10,000 ppm of various organic components usually present in this type of purges, if distillation is of the conventional type. The recovered anhydrified acetic acid flowed out from the bottom of the column for the recycle to the oxidation zone, and contained only 3% by weight of water. The ternary diagram reported by FIG. 2, experimentally determined at 30° C., is concerning the miscibility and immiscibility of the compositions comprising water, methyl-acetate and isobutyl-acetate.

We claim:

1. In a process for the synthesis of terephthalic acid, comprising the oxidation of para-xylene in acetic acid solution, at a temperature of from 100° to 230° C. and at a pressure from 1 to 30 kg/cm$^2$, and in the presence of a catalytic system based on manganese, bromine and cobalt, whereby water is formed and methyl-acetate is by-produced during the oxidation, whereby solid terephthalic acid is separated from the mother liquor and whereby one withdraws from the oxidation zone a liquid which is obtained by condensing the vapors released during the oxidation and which are mainly consisting of acetic acid and water, the improvement for the recovery of the acetic acid solvent, the catalyst and the methyl acetate, comprising:

(a) feeding the liquid obtained by condensing the released vapors and said mother liquor to an azeotropic distillation system in which the azeotropic agent is isobutyl-acetate;

(b) condensing the light ends of the azeotropic distillation, which are richer in water, and separating them into an aqueous phase and an organic phase, wherein the aqueous phase, which is lower and contains isobutyl-acetate and methyl-acetate, is conveyed to a stripping zone, whereby isobutyl-acetate and methyl-acetate are recovered, and wherein the organic phase is recycled to the azeotropic distillation system.

2. An improved process according to claim 1, wherein the reflux ratio between the amount of isobutyl acetate recycled with said organic phase and the amount of water in said light ends is from 4:1 to 14:1.

3. An improved process according to claim 2 wherein the reflux ratio is from 6:1 to 10:1 by weight.

4. An improved process according to claim 1, wherein in the distillation is carried out firstly in a partially anhydrifying column and wherein the stream richer in water, coming from the top of the column, is fed to a second column, in which the distillation is carried out in the presence of the azeotropic entrainer, isobutyl acetate, whereby the stream which leaves the bottom of the second column contains no more than 5% with respect to the acetic acid, and is recycled to the oxidation zone.

5. An improved process according to claim 1 wherein the stream which leaves the second column contains 3% by weight of water.

6. An improved process according to claim 1, wherein the light ends of said stripping are partially condensed and sent to a separating tank, in which the vapours, substantially consisting of methyl-acetate, separate from the liquid phase containing isobutyl-acetate, which is recycled.

7. An improved process according to claim 6 wherein methyl-acetate, at a titre of at least 90% by weight, is recovered through consecutive condensations, from the light ends of the stripping.

* * * * *